United States Patent [19]

Emery et al.

[11] 4,004,980

[45] Jan. 25, 1977

[54] ENZYME ENTRAPPMENT WITH CELLULOSE ACETATE FORMULATIONS

[75] Inventors: Alden H. Emery; Henry C. Lim, both of West Lafayette; Michael J. Kolarik, South Charleston, all of W. Va.

[73] Assignee: Purdue Research Foundation, West Lafayette, Ind.

[22] Filed: Mar. 25, 1975

[21] Appl. No.: 561,685

[52] U.S. Cl. .................................... 195/68; 195/63; 195/DIG. 11

[51] Int. Cl.² ......................................... C07G 7/02

[58] Field of Search ................. 195/63, 68, DIG. 4; 106/196; 264/200, 207; 260/227, 230

[56] References Cited

UNITED STATES PATENTS

| | | | |
|---|---|---|---|
| 1,891,146 | 12/1932 | Diamond | 264/207 X |
| 3,386,842 | 6/1968 | Hay | 106/196 X |
| 3,520,874 | 7/1970 | Ueno et al. | 106/196 X |
| 3,567,809 | 3/1971 | Ueno et al. | 106/196 X |
| 3,715,277 | 2/1973 | Dinelli et al. | 195/68 X |
| 3,875,008 | 4/1975 | Yoshino et al. | 195/68 X |

*Primary Examiner*—David M. Naff
*Attorney, Agent, or Firm*—John R. Nesbitt

[57] ABSTRACT

Enzymes are entrapped by preparing a polymer formulation containing cellulose triacetate and cellulose diacetate or glucose pentaacetate, adding an enzyme to the formulation, extruding the enzyme-containing formulation to form a solid matrix and soaking the solid matrix in an aqueous solution of acetone to swell and increase the permeability of the solid matrix.

8 Claims, 15 Drawing Figures

ACTIVITY OF SWELLED CELLULOSE TRIACETATE FIBERS.

ACTIVITY OF SWELLED 20% CELLULOSE DIACETATE FIBERS.

ACTIVITY OF SWELLED 50% CELLULOSE DIACETATE FIBERS.

ACTIVITY OF SWELLED 80% CELLULOSE DIACETATE FIBERS.

ACTIVITY OF SWELLED 20% GLUCOSE PENTAACETATE FIBERS.

ACTIVITY OF SWELLED 50% GLUCOSE PENTAACETATE FIBERS.

STABILITY OF CELLS TREATED WITH SOLVENTS.

EFFECT OF CELL CONCENTRATION ON CELL STABILITY AT 60°C.

STABILITY OF CELLS IN SUBSTRATE.

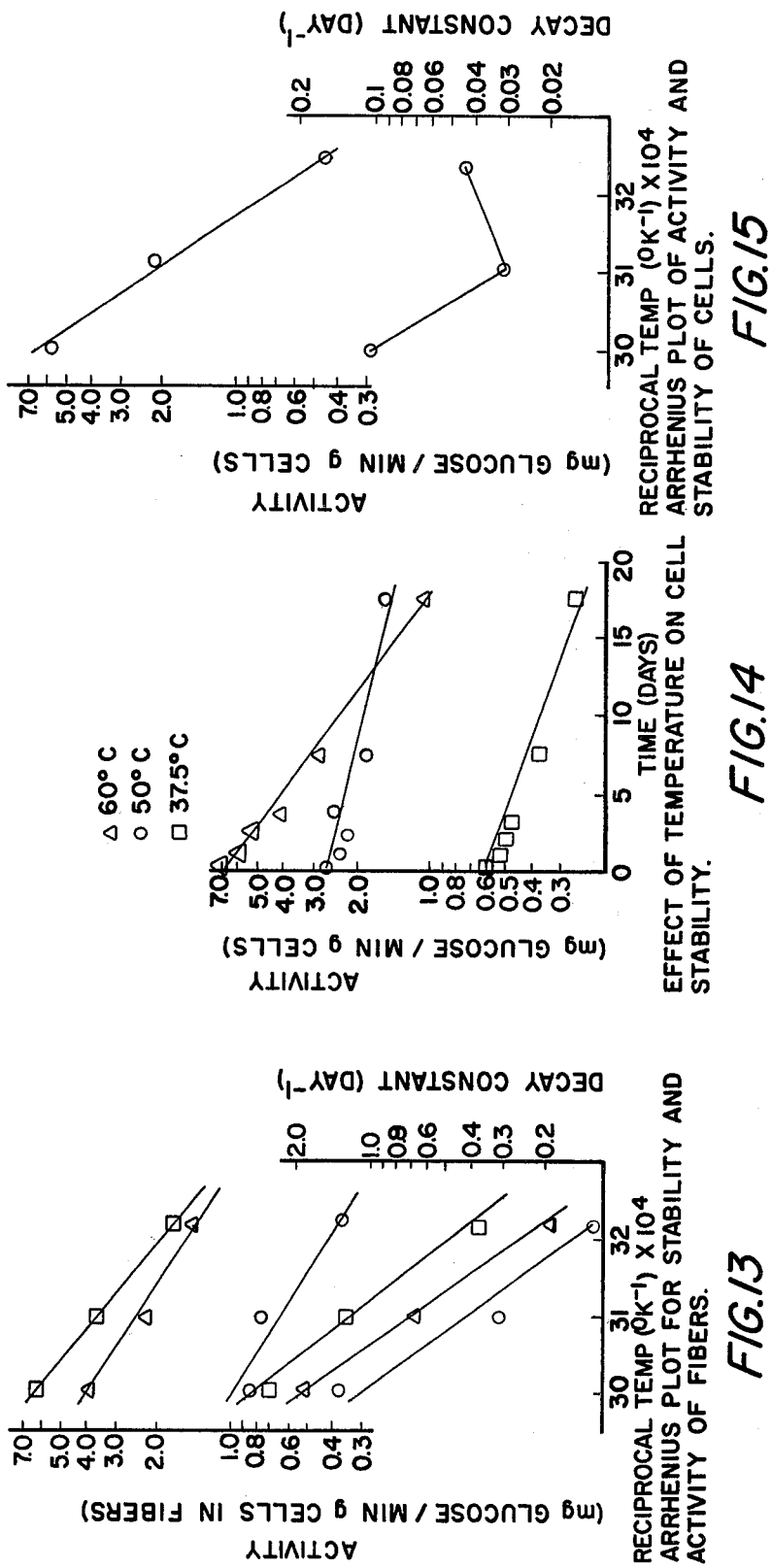

ENZYME ENTRAPPMENT WITH CELLULOSE ACETATE FORMULATIONS

FIELD OF THE INVENTION

This invention relates to an apparatus and method for entrapping enzymes and, more particularly, relates to chemical reactors containing immobilized enzymes, formulations, and methods for forming the same. The Government has rights in this invention pursuant to Grant No. GI-34919 awarded by the National Science Foundation.

BACKGROUND OF THE INVENTION

Enzymes are used industrially for many purposes, including the hydrolysis of starch, the breakdown of protein, and the isomerization of glucose to fructose. For years this use has involved soluble enzyme, which is lost after one use. In the past five years there has arisen a new industrial use of the technology in which enzymes are immobilized, usually to a solid material. This allows many uses of the enzyme and leads to greater economy.

The chief methods of immobilization are adsorption, covalent bonding, entrapment in a polymer, and entrapment inside the cell membrane. With respect to the prior art a group of patents have been heretofore issued in Italy and Germany to D. Dinelli, and assigned to SNAM Progetti and are directed to the entrapment of enzymatically active materials in cellulose acetate. This group of patents, however, appears not to involve second solid phases added to the formulation and further appears not to involve subsequent swelling after formation of a solvent not completely aqueous. It is therefore felt that the prior art has not completely solved the problems in this area, at least not for all intended applications.

SUMMARY OF THE INVENTION

This invention provides an apparatus and method for entrapping enzymes and includes a reactor, formulations, and methods relating to chemical reactors containing immobilized enzymes, with particular formulations of cellulose acetate (including addition of second solid phases thereto) and subsequent swelling treatments increasing the apparent activity of the entrapped enzymatic material without decreasing the stability of the same.

It is therefore an object of this invention to provide an improved apparatus and method for entrapping enzymes.

It is another object of this invention to provide a chemical reactor containing immobilized enzymes.

It is another object of this invention to provide an improved reactor formulation including addition of second solid phases.

It is still another object of this invention to provide an improved method for forming a chemical reactor containing immobilized enzymes.

It is yet another object of this invention to provide a chemical reactor that includes a particular formulation subjected to subsequent swelling treatments to increase the apparent activity of entrapped enzymatic material without decreasing the stability of the same.

It is still another object of this invention to provide cellulose triacetate in solid form that has added thereto a second solid material and dissolved in methylene dichloride and extruded through an orifice into a toluene bath to form a fiber or film that is subjected to swelling to thereby increase the permeability of the fiber or film for superior performance.

With these and other objects in view which will become apparent to one skilled in the art as the description proceeds, this invention resides in the novel apparatus, reactor, formulation, and method, substantially as hereinafter described, and more particularly defined by the appended claims, it being understood that such changes in the precise embodiment of the herein disclosed invention is meant to be included as come within the scope of the claims.

BRIEF DESCRIPTION OF THE DRAWINGS

The accompanying drawings illustrate the invention by means of a series of graphs, the drawings including FIGS. 1 through 15.

DETAILED DESCRIPTION OF THE INVENTION

Figure 1:
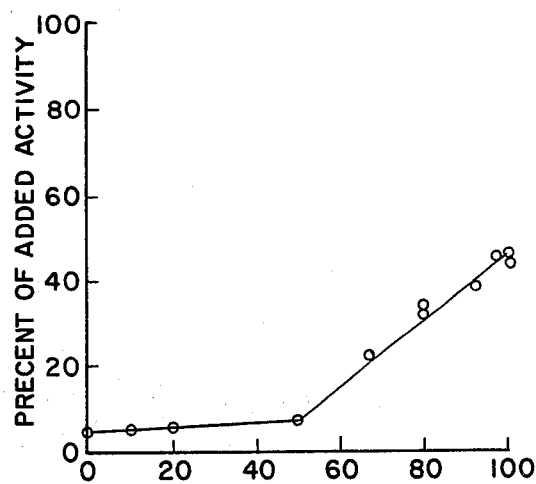

Basically, this invention requires formation of a solid phase in fiber or film form and swelling of the fiber or film after formation of the same. Several formulations and degrees of swelling have been achieved and tested.

In forming the solid phase, the basic polymer used was cellulose triacetate. The cellulose triacetate has included therewith a second solid material which is carried with the triacetate which is then dissolved in methylene dichloride and spun through an orifice into a toluene bath to form the basic fiber. Two kinds of solid materials were utilized, including glucose pentaacetate (which was then dissolved out of the fiber by soaking in acetone and which produces a larger permeability than available with cellulose triacetate alone) and cellulose diacetate (which has a higher affinity for acetone and water and thus is capable of being swelled to a higher extent). While the diacetate was not dissolved out of the fiber, it contributed to a higher degree of swelling and larger permeability than available with cellulose triacetate alone.

In swelling the fiber after formulation of the same, the fibers were soaked in mixtures of acetone and water. The amount of swelling is a function of the solids used in the formulation and of the concentration of acetone in water. The soaking not only dissolves out constituents such as glucose pentaacetate, but also increases the permeability of the fiber by swelling it.

Hereinafter a series of experiments and/or examples are set forth to detail the invention.

For the following experiments and examples, materials utilized included cellulose acetates purchased from Eastman Kodak, usually triacetate, in the flake form, as well as a secondary acetate powder designated as E-383-40. In addition, glucose pentaacetate was synthesized in two batches following a procedure designed to give the $\beta$-form (73), with the first batch having a melting point range of 130°–131° C and used in work carried out with whole cells, and the second batch having a melting point range of 129°–130° C and used in work carried out with partially purified enzymes. The solvents used were reagent quality acetone, toluene, and methylene chloride, while two sources of glucose isomerase enzyme were used in this work, one of which was a whole cell preparation that had been treated to fix the enzyme to the interior of the cell (obtained from NOVO Enzyme Corporation and designated as SP-92 and believed to be a species of *Bacillus bacteria*) and the other of which was a partially purified enzyme mixed with substantial amounts of filter aid and soluble. The buffer used in this work was 0.01 M succinate, pH 6.5.

Preparation of a Polymer-enzyme Solution

In a beaker 10. g of cellulose triacetate were dissolved in methylene dichloride to bring the total volume to 100 ml. In a separate beaker 5 g of whole cells were slurried in 15 ml of distilled water. The whole cell solution was then poured into the acetate solution under vigorous agitation. The result was an emulsion of the aqueous phase in the organic phase. This mixture was stirred for an additional five to thirty minutes, then formed into fibers or films as described in detail below.

When the partially purified enzyme was used, the procedure was modified slightly. For each gram of cellulose acetate or its substitute, 2.0 g of the enzyme were dissolved in 8.0 ml of water. The mixture was centrifuged to spin down the filter aid and the brown liquid layer was removed. Three milliliters of the brown solution were added to each ten ml of the acetate solution of the above procedure.

Preparation of Fibers

Fibers were formed from the polymer-enzyme solution by a wet spinning technique. A 10 ml hypodermic syringe was filled with the polymer-enzyme solution, and then was used to extrude the solution through a number 20 hypodermic needle into 100 ml of toluene held in a 100 ml graduated cylinder. The needle had been cut blunt for this use.

During the extrusion process the coagulating fiber would form ringlets about 2. cm in diameter which slowly settled to the bottom of the graduated cylinder. The rate of extrusion was controlled to give a continuous strand of the above ringlets at a rate slow enough to keep them from sticking together at the bottom of the graduated cylinder. Faster rates of extrusion gave smaller ringlets that tended to stick together while slower rates gave larger ringlets that did not settle properly.

Sometimes it was necessary to adjust the amount of methylene dichloride in the polymer-enzyme solution to have the extrusion process proceed smoothly. If too little solvent was present, the syringe was very hard to work with, while, if too much was present, the fiber strand would not form but rather a gooey mess would result on the hypodermic needle. With too much solvent, droplets would form, however, the graduated cylinder was not tall enough to allow enough of the methylene dichloride to be extracted from the drops to allow beads to form.

After the polymer-enzyme solution had been extruded into the toluene bath, the fibers were removed and air-dried before use. The air-dried fibers generally consisted of ribbons measuring 250 × 500 microns.

Preparation of Films

Films, or membranes, were formed by simply pouring some polymer-enzyme solution onto a flat glass plate and then spreading the solution into a thin layer which was allowed to air dry. A glass rod was used to spread the solution. A piece of paper at each end of the glass rod was used to adjust the thickness of the layer. The resulting films are generally 10–20 microns thick.

Measurement of the Enzyme Activity of Solid Matrices (Fibers and Films)

In all cases the enzymatic activity of a preparation was determined by measuring the rate of generation of glucose from 0.1 M fructose. The enzyme from the two different sources required slightly different concentrations of salts as activators and stabilizers. With the whole cells, 0.001 M $Co^{++}$ and 0.01 M $Mg^{++}$ were added to the assay cocktail. In all cases the buffer was 0.01 M succinate at pH 6.5.

Typically a known weight of a solid matrix, such as a fiber or film, was placed in test tube containing 9. ml of assay cocktail that lacked fructose. The test tube and its contents were placed in a constant temperature bath for 10–20 minutes to allow thermal equilibrium to be established. In the meantime, a 1.00 M fructose solution was also placed in the bath to allow it to warm before 1.0 ml was added to the test tube that contained the fiber or film.

After fructose was added to the assay mixture, seven or eight minutes were allowed to elapse before sampling was initiated. Samples were removed with an 0.1 ml syringe at five or ten minute intervals over a thirty to sixty minute time period, respectively. The glucose content of the samples was then determined by the procedure given below.

Assay of Glucose

The glucose concentration of the samples was determined with the glucose oxidase-peroxidase method using o-dianisidine as a dye. Samples were incubated at 40° C for a sufficient time to react all of the glucose present in the sample. At the end of the incubation time an equal volume of 60% $H_2SO_4$ was added to stabilize the color that had developed during the incubation period. The resulting color was measured at 525.5 nm on a Coleman 124 Spectrophotometer.

Studies on the Entrapment of Whole Cells

The purposes of this work were twofold. It was desired to improve the permeability of cellulose acetate under conditions that would allow entrapped enzymes to remain active. Also, it was desired to evaluate the suitability of using the resulting entrapped enzyme as a catalyst for the industrial isomerization of glucose to fructose.

The Effect of Swelling the Fiber After it Was Formed

Experiments were conducted in an effort to increase the permeability of the fiber by swelling it after it had been formed. In some of the earlier experiments it had been noted that acetone caused cellulose triacetate to swell even though it was not a complete solvent for the triacetate. The intent of the experiment was to swell the formed fiber in an acetone solution, and then to put the swelled fiber into a water solution in an effort to replace some of the acetone with water. It was hoped that the hydrated fiber would be more permeable.

In the experiment 0.08 g of fibers were placed into each of a series of test tubes which contained 10. ml of solution consisting of various fractions of acetone and water. The fibers were allowed to swell overnight (8 hours) before the acetone-water solution was poured off and replaced with distilled water. After 4–6 hours the fibers were assayed to determine the fraction of the added enzyme activity that could be observed.

FIG. 1 summarizes the results that were obtained with fibers that has been extruded through a number 20 hypodermic needle. Very little effect of swelling was noted until the swelling solution was composed of more than 50% acetone. As the acetone composition increased above 50% the fraction of the enzyme activity that could be observed increased linearly until the swelling solution contained 99% acetone. Fibers swelled in a solution containing 99% acetone showed slightly less enzyme activity because the fiber has started to deteriorate. Some of the fiber may have dissolved as a small amount of cells were observed at the bottom of the test tube after swelling.

A similar experiment was carried out with fibers extruded through a number 23 hypodermic needle with swelling solutions containing up to 80% acetone. Although the fibers from the number 23 needle were observed to have a smaller diameter than the fibers extruded from the number 20 needle, the fraction of the added enzyme activity that could be observed was the same for the two sets of fibers for each composition of swelling solution except one. The 67% acetone solution resulted in fibers that showed 29.6% of the added activity instead of 21.1%.

The Effect of Substituting Cellulose Diacetate (CDA) for a Portion of the Cellulose Triacetate Once it was known that acetone would swell cellulose triacetate fibers, it was felt that replacing a portion of the cellulose triacetate with an acetone soluble compound would result in a fiber that would have improved swelling properties. Cellulose diacetate is soluble in acetone and was selected for use.

Figure 2:
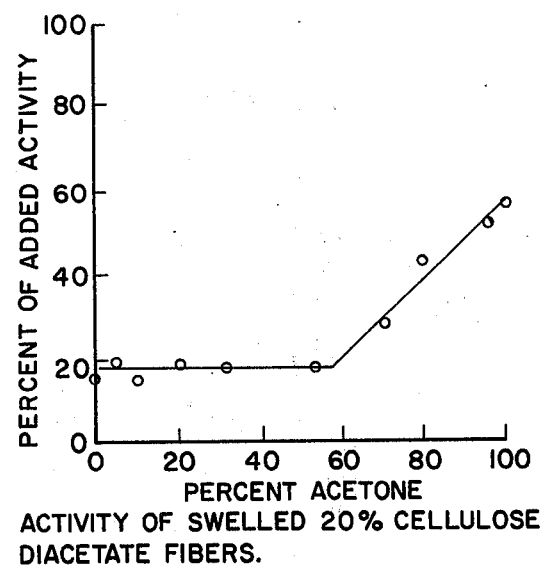
Figure 3:
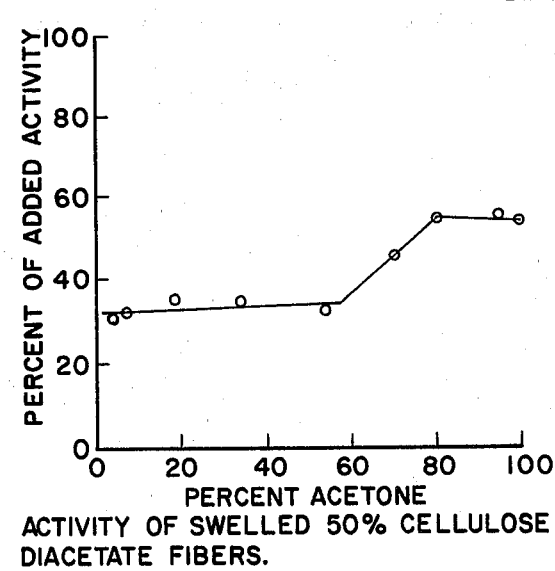
Figure 4:
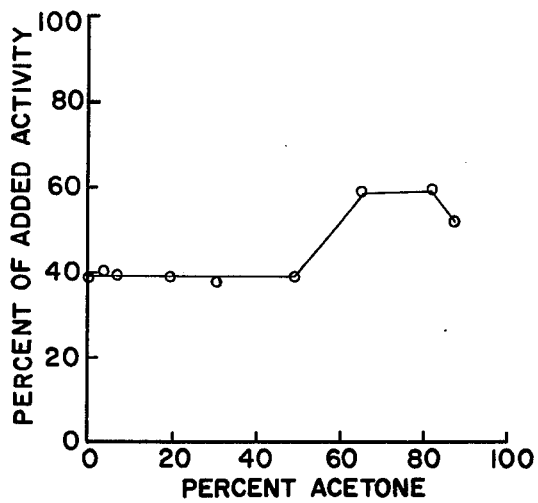

In the experiment, fibers were formed with 20, 50, and 80 percent of the cellulose triacetate replaced by cellulose diacetate. Samples of each fiber were swelled and assayed as in the previous experiment. The results for the fibers containing 20% CDA are summarized in FIG. 2, while the results from the fibers containing 50% CDA are shown in FIG. 3, and the results from the fibers containing 80% CDA in FIG. 4.

As the CDA content of the fibers increased, the fraction of the added enzyme activity that could be observed was increased for low values of acetone in the swelling solution.

In all cases, 50% acetone in the swelling solution appeared to be a critical value. For smaller fractions of acetone very little effect was observed due to swelling. At larger fractions of acetone, the fraction of the added activity that could be observed first increased, reached a maximum, then decreased as the fiber started to deteriorate.

In all cases the largest fraction of the added activity that could be observed was about 58%. As the CDA content of the fiber increased, the maximum fraction of the observed activity was achieved with smaller amounts of acetone in the swelling solution, and also deterioration occurred with smaller amounts of acetone.

The Effect of Substituting Glucose Pentaacetate (GPA) For a Portion of the Cellulose Triacetate A somewhat different approach to increase the permeability of the fiber was tried by replacing a portion of the triacetate with glucose pentaacetate. Glucose pentaacetate is a relatively small molecule, and when the fiber containing pentaacetate is put to swell, the small molecule could dissolve out of the matrix of the fiber leaving a hole behind. It was hoped that the resulting fiber would have higher permeabilities than the other preparations.

In the experiment fibers were made with 20% and 50% of the CTA replaced by GPA. The fibers were swelled as in the swelling experiment, then assayed to determine the fraction of the added enzymatic activity that was observable.

Figure 5:
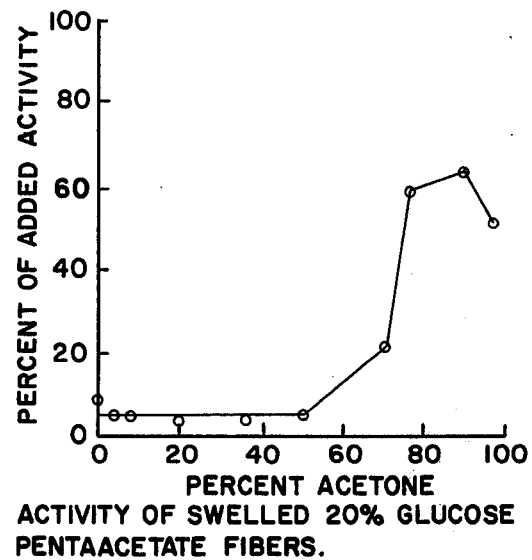
Figure 6:
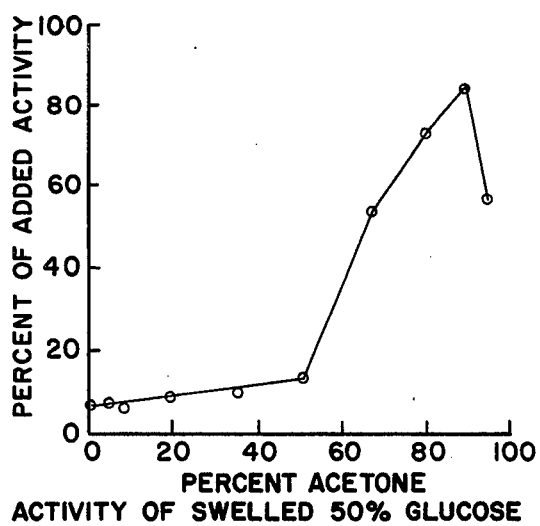

FIG. 5 summarizes that the results obtained with fibers containing 20% GPA while FIG. 6 summarizes the results obtained with 50% GPA. The results have similarities to the earlier results. Fifty percent acetone in the swelling solution again appeared to be a critical value. At lower amounts of acetone not much effect of swelling was observed. At higher values, the fraction of the observed activity increased, reached a maximum, then decreased as the fiber deteriorated.

The maximums were higher than for other preparations. The fiber formed with 20% GPA showed as much as 65% of the added enzymatic activity and the fiber containing 50% GPA showed as much as 82% of the added activity.

The Effect of Operating Temperature on The Activity and Stability of Entrapped Enzymes Experiments were carried out to study the effect of operating temperature on the activity and stability of the entrapped enzyme. It has been theoretically found that the productivity of an entrapped enzyme should increase as the operating temperature is decreased, and it was desired to verify that prediction. The stability characteristics of an entrapped enzyme were also studied. Finally, it was desired to compare the productivity of the entrapped enzyme to the productivity of the same enzyme when used in a batch process without being immobilized.

In the experiment, samples of 0.05 g of fibers that had 50% of the CTA replaced by GPA were swelled in 0, 67 and 90 percent acetone, respectively, and then placed in batch reactors at 40°, 50°, and 60° C. The samples were covered with assay cocktail and assayed. (40° C was actually 37.5° C).

To carry out an assay, on subsequent days the reaction mixture from the previous day was poured from the reactor that contained the fibers. The reactor and fibers were washed with distilled water before 9.0 ml of a fresh assay cocktail, lacking fructose, was added. The reactor was returned to a constant temperature bath at the appropriate temperature of 20–30 minutes. 1.0 ml of 1.0 M fructose was added to initiate the assay. Samples were collected at 5–10 minute intervals over a 30–60 minute time period.

When sampling was completed, the reactor and its contents were left open to the atmosphere in the constant temperature bath until the next day when the assay procedure was repeated. The enzyme activity present in the fibers was determined from the rate of generation of glucose from fructose.

Figure 9:
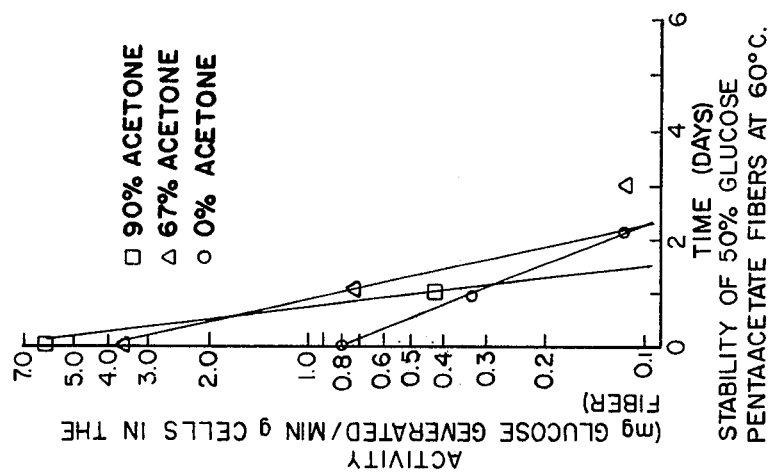
Figure 8:
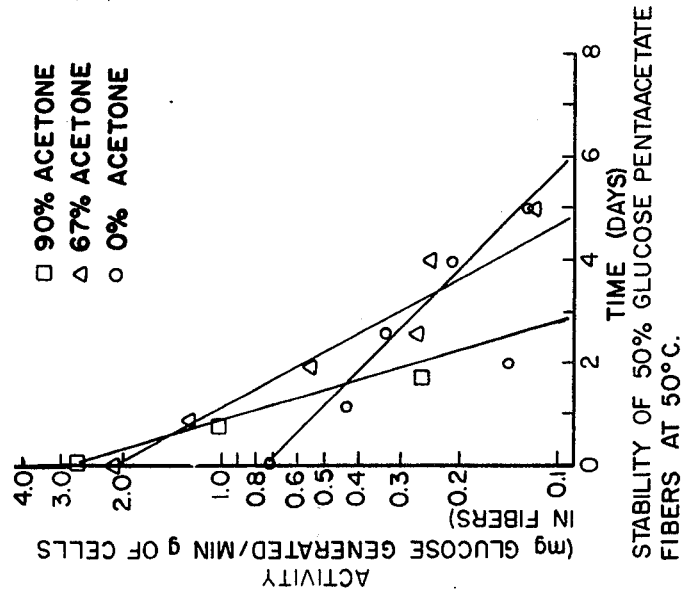
Figure 7:
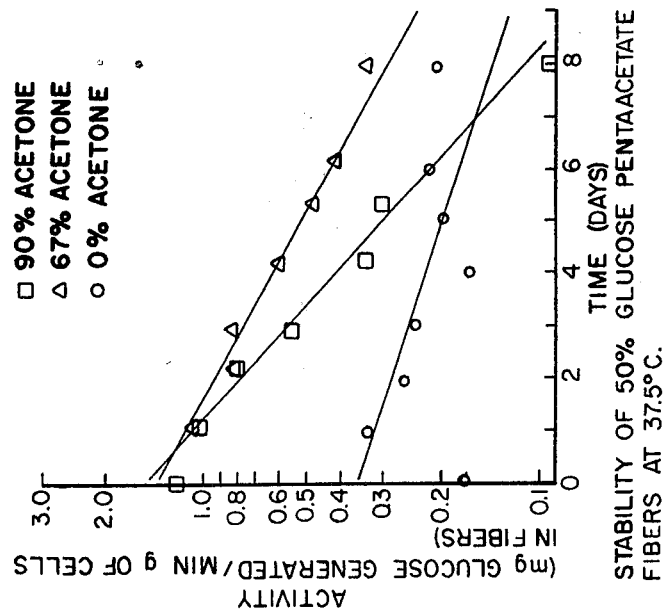

FIGS. 7, 8 and 9 summarize the results obtained at 40°, 50° and 60° C respectively. At 40° C there appeared to be some sort of incubation period as the samples at that temperature had higher activities on the second day than on the first day. An incubation period was not observed at the higher temperatures.

At all three temperatures the fibers swelled in 90% acetone had the highest activities and the highest decay rates, while the samples swelled in 0.0% acetone had the lowest activities and the lowest decay rates. As the temperature was increased from 40° C both the activity and the decay rates increased. After the first day the samples at 40° C followed a first order decay, as did the samples at the higher temperatures.

At all three temperatures the fibers lost their catalytic activity much faster than had been expected. Some earlier work carried out on the stability of whole cells of the type put into the fiber indicated that cells stored at 60° C might retain half of their activity after 30 days. At lower temperatures, the cells would be expected to last longer. In the experiment at 60° C the cells in the fibers has lost more than one-half of their activity in one day. Even at 40° C the half-life was less than a week. Some later experiments indicated the poor stability was a result of some inherent characteristics of the enzyme rather than as a result of any of the treatments in the preparation of the swelled fibers. A discussion of the stability of the cells appears later.

Table 1

| Fiber | The Decay Constants For The Various Fibers Temperature | | |
|---|---|---|---|
| | 37.5° C | 50° C | 60° C |
| 0% | 0.124 day$^{-1}$ | 0.346 | 1.35 |
| 67% | 0.198 | 0.648 | 1.63 |
| 90% | 0.332 | 1.21 | 2.66 |

Table 1 summarizes the first order decay constants that were calculated from the experimental data. It has been theoretically determined that when internal diffusion was limiting the rate of reaction, an enzyme would appear to decay at slightly more than one-half the true rate. In the table of decay constants (Table 1), it can be seen that there was a difference of more than a factor of two between the decay rates for the fibers which had no acetone in the swelling solution and the fibers which had 90% acetone in the swelling solution.

Since there was more than a factor of two difference in the decay rates, at all three temperatures, the inference was that some other cause was responsible for the loss of activity other than thermal denaturation. Also, since the enzyme has lost its activity at different rates for fibers that had different swelling treatments, it was indicated that either the swelling treatment was responsible for causing some loss of activity or that different degrees of swelling (and hence different permeabilites) caused the differences in the observed rates of decay.

Experiments were carried out to determine whether the acetone swelling solution had a damaging effect on the stability of the enzyme in the whole cells. In the experiment cells were covered with pure acetone for several hours while the acetone was allowed to evaporate. The cells were then used to prepare a solution of 0.005 g cells per ml of water. No salts, buffer, or substrate were added to these solutions. The solution was placed in a 60° C temperature bath for the duration of the study. Samples of the cell solution were removed daily and assayed to determine their catalytic activity. Similar solutions were prepared with cells that had not been covered with acetone for a control and with cells that has been covered with toluene or methylene dichloride to obtain information on those materials also.

Figure 10:
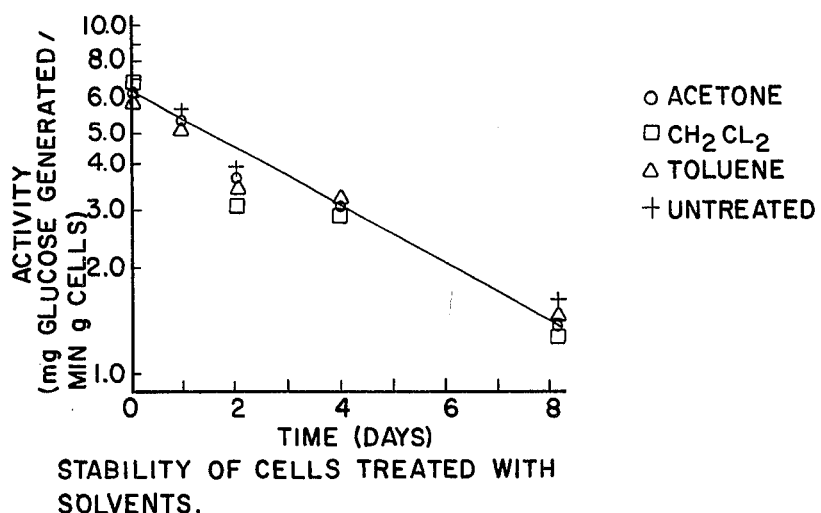

FIG. 10 shows the results obtained from the experiment. There was no observable difference in the activity or stability of any of the solutions. However, all the samples lost their activity faster than in the earlier experiment with a solution that had a higher concentration of cells.

The conclusion from the experiment was that acetone in the swelling solution was not responsible for the observed high rates of decay in the fiber stability experiment.

One of the ways the swelled fiber could have lost its activity during the stability experiment was by shrinking. As the fiber shrank, less of the enzyme activity would have been observed even though the enzyme has not actually lost its activity.

One of the experiments carried out was to determine if it would be possible to reactivate by a second swelling the fiber that had lost its activity. Some fibers that had been made with CTA only and that has been swelled in 80% acetone were allowed to sit in assay cocktail at 60° C until the fibers showed only 5.9% of the activity that has been added to them. On their first assay, the fibers has showed 35% of the added activity. The fibers were reswelled in 80% acetone and reassayed, at which time the apparent activity had fallen to 5.0%.

The conclusion from the experiment was that reswelling would not reactivate the fiber. The inference drawn from the study was that the fibers lost their activity because the enzyme in them has lost its activity.

Since the degree of swelling which a fiber received had an effect on the stability of the enzyme in the fiber, it was postulated that either a poison was diffusing into the fiber or a component essential to the activity of the enzyme was diffusing out of the fiber. It was reasoned that if a component essential to the activity of the enzyme was diffusing out of the fiber, the cells would have different activities or different stabilities when stored at different concentrations. The enzyme was pictured as undergoing a dissociation reaction as follows:

$$E \rightleftharpoons E' + G \qquad (1)$$

where: $E$ is an active enzyme molecule
$E'$ is an inactive enzyme molecule
$G$ is a group essential to the enzyme activity
The equilibrium constant for the reaction is the following $$K_{eq} = \frac{[E'] [G]}{[E]} \qquad (2)$$

Since the numerator of the equilibrium constant is second order while the denominator is first order, the fraction of the enzyme that would have dissociated at equilibrium would depend upon the initial concentration of enzyme. Dilute solutions would dissociate more than concentrated solutions.

If the equilibrium was achieved very quickly after a solution of enzyme was made up, then a dilute solution would show smaller specific activity than a concentrated solution, while if the equilibrium was slow in occurring, maybe requiring several days to be achieved, dilute solutions would lose their activity faster than concentrated solutions, but they would have the same specific activity initially. Enzyme would, therefore, lose its activity by dissociation in addition to the normal thermal denaturation.

Figure 11:
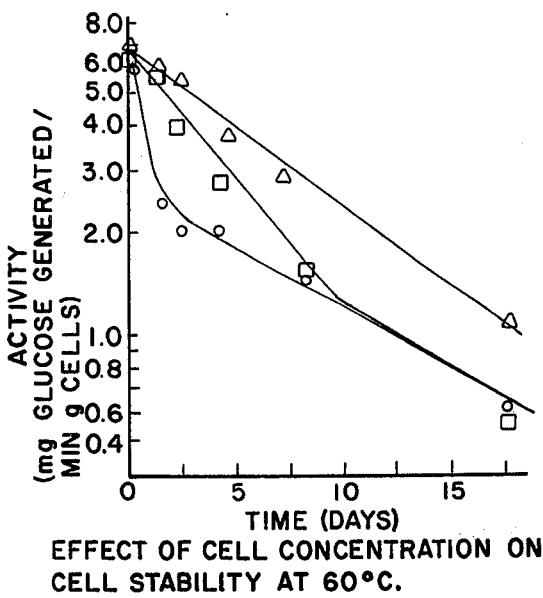

An experiment was carried out to determine the effect of cell concentration on the stability of the enzyme activity by storing solutions of cells containing 0.05, 0.005, and 0.0005 g cells/ml at 60° C. Samples were removed from the solutions daily and were assayed to determine their specific activity. In the experiment the cells were dissolved in distilled water, and no salts, buffer, or carbohydrates were added. However, buffer and salts are present in the cells as they are supplied. FIG. 11 summarizes the results that were obtained from the experiment. Clearly, the stability of the cells was dependent upon the concentration at which they were stored.

Although $Co^{++}$ and/or $Mg^{++}$ could have been the dissociating group G of Equation 1, work carried out by co-workers would indicate that such was not the case.

At the lowest concentration of cells, two-thirds of the enzyme activity was lost in one day. This concentration corresponds to the concentration of cells that would have resulted in the earlier experiment with fibers if the cells in the fibers were spread homogeneously in the assay cocktail. Also, the effect of substrate was to increase the rate at which the cells lost their enzyme activity, as explained below.

Figure 12:
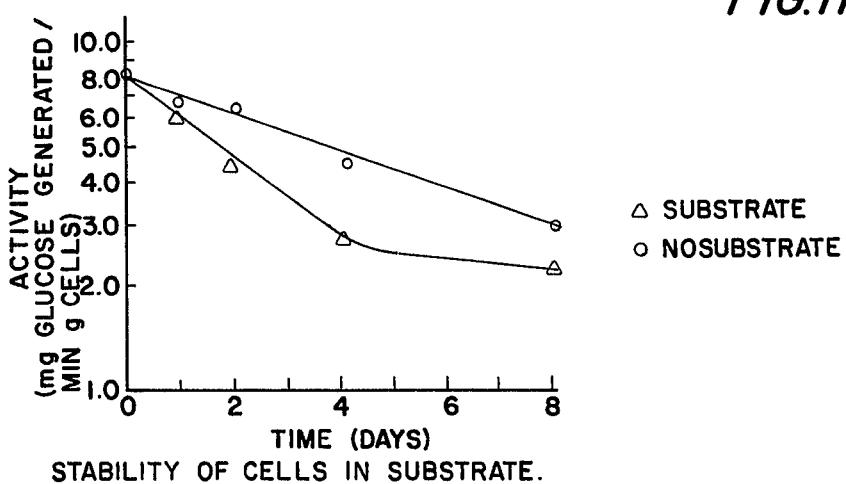

An experiment was carried out to determine the effect of 0.1 M glucose-fructose solution on the stability of the cells. FIG. 12 summarizes the results obtained, along with the reults for a similar concentration without substrate. The concentration of cells used was 0.05 g/ml. The cell solution with substrate present lost its activity at about twice as fast as the solution without substrate.

The fibers which were swelled in 90% acetone lost their activity faster than the cell solution at the lowest concentration, while the fibers swelled in 0.0% acetone lost their activity more slowly. The conclusion drawn from the experiment was that the cells has lost their activity at about the same rate as the fibers, especially when the effect of substrate on the rate of deactivation of the cells was considered.

As a result of the stability study of fibers, it was possible to determine the apparent energy of activation for both the forward reaction and denaturation at each swelling condition. FIG. 13 is an Arrhenius plot of the initial activity and the first order decay rate for the fibers. From the lines drawn on the plot, the energies of activation were calculated. Table 2 gives the results of the calculations along with the energy of activation for the cells themselves. FIGS. 14 and 15 are the stability data and the Arrhenius plot for the cells.

Table 2

| System | Energies of Activation. | |
|---|---|---|
| | Initial Activity | Denaturation |
| 0.9 | 12,800 cal/g mole | 19,300 |
| 0.67 | 9,200 | 19,300 |
| 0 | 9,200 | 19,300 |
| cells | 22,600 | |

Since the energy of activation of the reaction from the cells was much higher than from the fibers, it would appear that considerable diffusional resistance was still present in the fibers even after swelling. However, the lowest energy of activation that should have been observed based on diffusion limitations was slightly more than one-half the value from the cells. The calculated values from fibers swelled in 0.0 and 67% acetone were somewhat lower than one-half the value for cells, but this is unexplained at this time.

Even the fibers swelled with 90% acetone had an energy of activation only slightly more than one-half the value for cells. This was surprising since, at 60° C, the initial activity of the fiber was equivalent to 88% of the activity put in the fiber. Since the activity of the fibers did not decrease with temperature as fast as the activity of cells alone, more activity was observed at lower temperatures than was considered to have been put into the fibers. At 50° C the activity observed in the fibers was equivalent to 126% of the activity of the weight of cells that were put into the fiber. At 37.5° C it amounted to 190%. It was not known why.

Also, as a result of the stability study on fibers, it was possible to determine the amount of product that could be obtained from the fibers during their useful life based on a first order decay model. Table 3 summarizes the product that could be obtained for the three swelling treatments at three temperatures.

Table 3

| System | Product Obtainable From Fiber. | | |
|---|---|---|---|
| | Temperature | | |
| | 37.5 | 50 | 60 |
| 0% | 4.1 | 3.03 | 0.88 |
| 67% | 10.2 | 4.90 | 3.35 |
| 90% | 6.56 | 4.04 | 3.29 |

As the operating temperature decreased, the amount of product obtainable increased as predicted by the earlier equations. The fibers swelled in 0% and 67% acetone more than doubled their productivity for each 10° decrease in operating temperature. The fiber swelled in 90% acetone doubled its productivity during the 20° decrease in temperature.

Summary for the Entrapment of Whole Cells

Whole cells were entrapped in cellulose triacetate formed into a coarse fiber. Swelling the fiber is an acetone-water solution was found to yield a fiber that permitted more of the enzyme activity to be observed than unswelled fibers when used in a chemical reactor. Substitution of glucose pentaacetate for some of the cellulose triacetate resulted in a fiber that allowed even more of the entrapped activity to be observed in a reactor.

Fibers formed with 50% glucose pentaacetate and 0.5 g of cells/g acetates were found to allow 82% of the entrapped enzyme activity to be observed in a reactor. The productivity of the fibers was evaluated experimentally. Lower temperatures allowed more product to be produced by the fibers than higher temperatures. With the cells and operating conditions used, the fibers did not appear to have a producing advantage over the free cells.

From the foregoing, it can be seen that, compared to cellulose acetate with no swelling, the formulations and fiber and film swelling disclosed herein enable increased activity without greatly increasing the rate of decay of activity of the fibers or film. This results in more product being produced for a given quantity of enzymatic material.

Concerning further development of the formulations herein disclosed, there are many solids that might serve the function of being able to be dissolved out, solids which are not soluble in toluene but are soluble in other solvents which do not damage the enzymatic material. Examples are sucrose octaacetate and maltose octaacetate. In addition there may be other polymers which increase the affinity for swelling fluids, but cellulose diacetate seems to be a natural selection for this purpose.

There also may be other solvents which will increase the permeability of the fibers. Acetone seems to be a good choice however in that it serves the role at low cost. Another possibility is methyl ethyl ketone.

Concerning industrial choices of immobilization methods generally, other materials might be used for entrapping, and manufacturers have suggested that polyacrylamide would be useful for this purpose. The high cost of polyacrylamide compared to cellulose acetate however seems to make it a less attractive alternative.

Entrapping is one of several methods of immobilizing enzymes, and any of the other methods, notably covalent bonding, adsorption, and entrapping in whole cells, might be utilized. The supports so far seriously considered and the binding techniques involved however are generally more expensive than the methods disclosed herein.

The method and apparatus for entrapping enzymes, reactor, formulations, and method of this invention is particularly useful when immobilization of an enzymatic material by inexpensive methods having reasonable properties is needed or required.

What is claimed is:

1. A method of forming an entrapped enzyme, said method comprising:
   providing cellulose triacetate in solid form;
   adding a second solid material to said cellulose triacetate, said second solid material being selected from the group consisting of cellulose diacetate and glucose pentaacetate;
   dissolving the cellulose triacetate and second solid material in a solvent;
   adding an enzyme to said cellulose triacetate and second solid material;
   extruding said dissolved cellulose triacetate and said second solid material through an orifice to form a solid matrix soluble in a swelling liquid and
   soaking said solid matrix in an aqueous solution of acetone and water containing between about 50 to 98% acetone for swelling said matrix to increase the permeability of the solid matrix.

2. The method of claim 1 wherein said second material is glucose pentaacetate and is added in solid form to said cellulose triacetate, said glucose pentaacetate being in the range of between 20 and 50% of said cellulose triacetate.

3. The method of claim 1 wherein said second material is cellulose diacetate and is added in solid form to said cellulose triacetate, said cellulose diacetate being in the range of between 20 and 80% of said cellulose triacetate.

4. The method of claim 1 wherein said cellulose triacetate and said second solid material are dissolved in methylene dichloride.

5. The method of claim 1 wherein said dissolved cellulose triacetate and second solid material are spun through an orifice to form a fiber.

6. The method of claim 1 wherein said dissolved cellulose triacetate and second solid material are cast through an orifice to form a film.

7. The method of claim 1 wherein said solid matrix is soaked in a mixture of acetone and water containing about 50% acetone.

8. A method of forming an entrapped enzyme, said method comprising:
   providing a mixture in liquid form of cellulose triacetate and a second material selected from the group consisting of cellulose diacetate and glucose pentaacetate with both said cellulose triacetate and said second material having been dissolved from solid form in solvent;
   adding an enzyme to said cellulose triacetate and second solid material;
   extruding said dissolved cellulose triacetate and said second solid material through an orifice to form a solid matrix soluble in a swelling liquid; and
   soaking said solid matrix in an aqueous solution of acetone and water containing between about 50 and 98% acetone for swelling said matrix to increase the permeability of the solid matrix.

* * * * *